US006559275B2

(12) United States Patent
Minami et al.

(10) Patent No.: US 6,559,275 B2
(45) Date of Patent: May 6, 2003

(54) METHOD FOR PRODUCING ALIPHATIC POLYESTER

(75) Inventors: Masato Minami, Kanagawa (JP); Shinya Kozaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/231,301

(22) Filed: Aug. 30, 2002

(65) Prior Publication Data

US 2003/0023026 A1 Jan. 30, 2003

Related U.S. Application Data

(63) Continuation-in-part of application No. 09/990,543, filed on Nov. 23, 2001, now abandoned.

(30) Foreign Application Priority Data

| Dec. 1, 2000 | (JP) | 2000-367302 |
| Dec. 5, 2000 | (JP) | 2000-370258 |
| Dec. 5, 2000 | (JP) | 2000-370259 |
| Apr. 12, 2001 | (JP) | 2001-114044 |
| Apr. 20, 2001 | (JP) | 2001-122694 |
| Apr. 20, 2001 | (JP) | 2001-122695 |
| Jul. 16, 2001 | (JP) | 2001-215391 |

(51) Int. Cl.$^7$ .................... C08C 19/20; C08H 5/04
(52) U.S. Cl. ............. 528/354; 528/357; 524/765; 524/768; 524/779; 524/783; 527/103; 527/300
(58) Field of Search ................ 528/354, 357; 524/765, 768, 779, 783; 527/103, 300

(56) References Cited

U.S. PATENT DOCUMENTS

| 3,437,668 A | 4/1969 | Koenig et al. ............ 260/343 |
| 5,136,017 A | 8/1992 | Kharas et al. ............ 528/354 |
| 6,420,513 B2 | 7/2002 | Minami ................... 528/354 |

FOREIGN PATENT DOCUMENTS

| GB | 1133247 | 11/1968 |
| JP | 54-73722 | 6/1979 |
| JP | 11-158172 | 6/1999 |

*Primary Examiner*—Samuel A. Acquah
(74) *Attorney, Agent, or Firm*—Fitzpatrick, Cella, Harper & Scinto

(57) ABSTRACT

The invention relates to a method for producing an aliphatic polyester, utilizing starch as a raw material. The invention produces an aliphatic polyester by the steps of hydrolyzing starch to obtain glucose, oxidizing the glucose to obtain gluconolactone or gluconic acid, reducing the gluconolactone or the gluconic acid to obtain caproic acid, chlorinating the caproic acid to obtain 6-chlorocaproic acid, cyclizing the 6-chlorocaproic acid to obtain ε-caprolactone, and executing ring-opening polymerization of the ε-caprolactone.

30 Claims, No Drawings

METHOD FOR PRODUCING ALIPHATIC POLYESTER

This is a continuation-in-part application of U.S. patent application Ser. No. 09/990,543 filed on Nov. 23, 2001 now abandoned.

BACKGROUND OF THE INVENTION

1. Field of the Invention

The present invention relates to a method for producing aliphatic polyester and a method for using glucans such as starch, cellulose etc. as a resource.

2. Related Background Art

The conventional general-purpose plastic products are composed of polymers synthesized from petroleum resources. More specifically, polymer products such as polyester, polystyrene, nylon, polyethylene, polyvinyl chloride, polyimide, polycarbonate etc. are all synthesized from petroleum. However, the petroleum is a limited resource which is to run out sooner or later. For this reason there is strongly desired a technology for producing the general-purpose plastic products from a new raw material capable of substituting petroleum, namely a recyclable raw material.

On the other hand, starch is a polymer compound formed by dehydration polymerization of D-glucose, and is an important polysaccharide comparable to cellulose. Starch is produced from potato, sweet potato, corn etc., with the worldwide production (production amount of corn) amounting to 400 to 500 million tons per year, and is a recyclable resource having the largest production amount among the natural resources. Starch can highly be expected as a new resource which replaces the petroleum, if general-purpose plastic products can be produced therefrom.

SUMMARY OF THE INVENTION

The object of the present invention is to provide a method for producing aliphatic polyester utilizing glucans such as starch or cellulose as a raw material.

Based on a standpoint that a novel technical development is required to provide against the exhaustion of the petroleum resources in the future, the present inventors through intensive investigation have noticed starch as a raw material which can replace petroleum and have found that aliphatic polyester can be synthesized from caproic acid that can be obtained from starch via glucose, thereby attaining the present invention. This finding opens up a way for utilizing starch as an efficient resource in obtaining plastics of high quality from starch as a starting material.

The above-mentioned object can be attained, according to an embodiment of the present invention, by a method for producing an aliphatic polyester represented by the following formula (I):

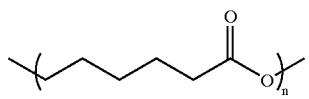
(I)

(wherein n stands for an integer within a range from 5 to 10,000), the method comprising the steps of:

(i) hydrolyzing starch to obtain glucose;

(ii) oxidizing the glucose to obtain gluconolactone;

(iii) reducing the gluconolactone to obtain caproic acid;

(iv) chlorinating the caproic acid to obtain 6-chlorocaproic acid;

(v) cyclizing the 6-chlorocaproic acid to obtain ε-caprolactone represented by the following formula (II):

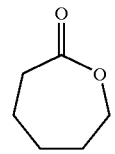
(II)

and (vi) executing ring-opening polymerization of the ε-caprolactone.

The aforementioned object can be attained also, in another embodiment of the present invention, by a method for producing an aliphatic polyester represented by the following formula (I):

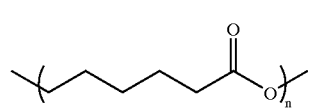
(I)

(wherein n stands for an integer within a range from 5 to 10,000), the method comprising the steps of:

(i) hydrolyzing starch to obtain glucose;

(ii) oxidizing the glucose to obtain gluconic acid;

(iii) reducing the gluconic acid to obtain caproic acid;

(iv) chlorinating the caproic acid to obtain 6-chlorocaproic acid;

(v) cyclizing the 6-chlorocaproic acid to obtain ε-caprolactone represented by the following formula

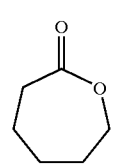
(II)

and (vi) executing ring-opening polymerization of the ε-caprolactone.

ε-caprolactone is a compound having an intramolecular cyclic ester structure and is well known as an industrially producible compound by oxidizing cyclohexanone. It is also known that ε-caprolactone easily undergoes ring-opening polymerization to provide aliphatic polyester (Japanese Patent Application Laid-Open No. 11-158172). However, there have not been known examples, except that of the present inventors, of synthesizing ε-caprolactone from starch and obtaining aliphatic polyester therefrom.

According to the present invention, there is also provided a method for producing an aliphatic polyester represented by the following formula (I):

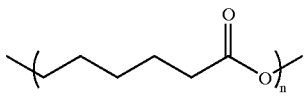

(wherein n stands for an integer within a range from 5 to 10,000), the method comprising the steps of:

(i) hydrolyzing glucan to obtain glucose;

(ii) oxidizing the glucose to obtain gluconolactone or gluconic acid;

(iii) reducing the gluconolactone or the gluconic acid to obtain caproic acid;

(iv) chlorinating the caproic acid to obtain 6-chlorocaproic acid;

(v) cyclizing the 6-chlorocaproic acid to obtain ε-caprolactone represented by the following formula (II):

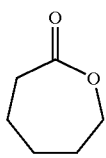

and (vi) executing ring-opening polymerization of the ε-caprolactone.

According to the present invention, there is also provided a method for producing an aliphatic polyester represented by the following formula (VI):

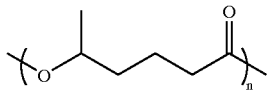

(wherein n stands for an integer within a range from 10 to 6,000), the method comprising the steps of:

(i) hydrolyzing glucan to obtain glucose;

(ii) oxidizing the glucose to obtain gluconolactone or gluconic acid;

(iii) reducing the gluconolactone or the gluconic acid to obtain caproic acid;

(iv) chlorinating the caproic acid to obtain 5-chlorocaproic acid;

(v) cyclizing the 5-chlorocaproic acid to obtain δ-caprolactone; and (vi) executing ring-opening polymerization of the δ-caprolactone.

DETAILED DESCRIPTION OF THE PREFERRED EMBODIMENTS

The method of the present invention for producing aliphatic polyester, in an embodiment thereof, comprises the steps of:

(i) hydrolyzing starch to obtain glucose;

(ii) oxidizing the glucose to obtain gluconolactone or gluconic acid;

(iii) reducing the gluconolactone or the gluconic acid to obtain caproic acid;

(iv) chlorinating the caproic acid to obtain 6-chlorocaproic acid;

(v) cyclizing the 6-chlorocaproic acid to obtain ε-caprolactone; and (vi) executing ring-opening polymerization of the ε-caprolactone to obtain aliphatic polyester represented by the foregoing formula (I).

The method for synthesizing aliphatic polyester from starch opens up a novel way of utilizing starch as a resource. From this standpoint, the method of the present invention for producing aliphatic polyester also provides a useful method for utilizing starch as a new resource.

In the following there will be explained each of the aforementioned steps (i) to (vi).

Step (i) (Starch to Glucose)

Conversion from starch to glucose can be achieved for example by hydrolysis with a dilute acid such as sulfuric acid, hydrolysis with an enzyme such as amylase or maltase, or hydrolysis with ultracritical water. The step of obtaining glucose from starch is preferably executed by hydrolysis with an acid. The reaction conditions can be suitably determined according to the already known method.

Step (ii) (Glucose to Gluconolactone or Gluconic Acid)

Conversion from glucose to gluconolactone can be achieved for example by bromine oxidation of glucose or by a method utilizing notatin which is a glucose oxidase. The step of obtaining gluconolactone from glucose is preferably executed by bromine oxidation. The reaction conditions can be suitably determined according to the already known method.

Conversion from glucose to gluconic acid can be achieved for example by oxidation with bromine and concentrated sulfuric acid, more specifically oxidizing and hydrolyzing glucose in sulfuric acid saturated with bromine, or by electrolytic oxidation of a glucose solution or by fermentation of gluconic acid utilizing bacteria of Penicillium family. The step of obtaining gluconic acid from glucose is preferably executed by oxidation utilizing bromine and concentrated sulfuric acid. The reaction conditions can be suitably determined according to the already known method.

Step (iii) (Gluconolactone or Gluconic Acid to Caproic Acid)

Conversion of gluconolactone or gluconic acid to caproic acid can be achieved for example by reduction thereof with hydroiodic acid and red phosphorus. In this reaction, it is desirable that the hydroxyl group alone of gluconolactone or gluconic acid is oxidized.

The amount of red phosphorus employed in the reduction is preferably 1.8 to 2.4 equivalents with respect to gluconolactone or gluconic acid. Hydroiodic acid employed in the reduction preferably has a concentration of 50 to 60 mass %, and is preferably employed in a weight of 40 to 60 times with respect to the weight of gluconolactone or gluconic acid. The reducing reaction is completed by refluxing gluconolactone or gluconic acid and red phosphorus in hydroiodic acid for about 20 hours. The reaction mixture is filtered, then the filtrate is extracted with ether and washed with an aqueous solution of sodium hydrosulfite of about 5 mass %, and caproic acid can be obtained by distilling the ether solvent and executing vacuum distillation.

Step (iv) (Caproic Acid to 6-Chlorocaproic Acid)

Conversion from caproic acid to 6-chlorocaproic acid can be achieved for example by chlorination with chlorine and concentrated sulfuric acid, preferably by chlorination conducted by reacting caproic acid with chlorine in concentrated sulfuric acid. The reaction conditions can be suitably determined according to the known method.

Step (v) (6-Chlorocaproic Acid to ε-Caprolactone)

Conversion from 6-chlorocaproic acid to ε-caprolactone can be achieved for example by cyclization utilizing an aqueous solution of sodium hydroxide, preferably by boiling 6-chlorocaproic acid in an aqueous solution of sodium hydroxide. The 5 reaction conditions can be suitably determined according to the known method.

Step (vi) (ε-Caprolactone to Aliphatic Polyester; Ring-opening Polymerization)

In the present invention, aliphatic polyester is synthesized by ring-opening polymerization of ε-caprolactone utilizing a compound having a hydroxyl group as an initiator normally in the presence of a catalyst. The initiator is used for opening the ring of ε-caprolactone, and the catalyst accelerates the polymerization by interacting with the ring-opened product.

Polymerization Catalyst

In the present invention, a known ring-opening polymerization catalyst can be employed as the polymerization catalyst in the ring-opening polymerization of ε-caprolactone. Examples of such catalyst include tin dichloride, tin tetrachloride, tetra-n-butoxy-germanium, tetramethoxy-germanium, tetraethoxy-germanium, triethoxy-aluminum, tri-n-propoxy-aluminum, tri-iso-propoxy-aluminum, tri-n-butoxy-aluminum, tri-iso-butoxy-aluminum, aluminum chloride, triethyl-aluminum, trimethyl-aluminum, di-iso-propyl zinc, dimethyl-zinc, diethyl-zinc, zinc chloride, tetra-n-propoxy-titanium, tetra-n-butoxy-titanium, tetra-t-butoxy-titanium, tetraethoxy-zirconium, tetramethoxy-zirconium, tetra-iso-propoxy-zirconium, tetra-n-butoxy-zirconium, tetra-iso-butoxy-zirconium, tetra-t-butoxy-zirconium, and organic compounds of rare earth metals such as La, Nd, Sm, Er, Tm, Yb or Lu. Such catalyst may be employed singly or as a mixture of at least two catalysts.

The amount of polymerization catalyst can be determined suitably, but is usually within a range of 0.01 to 10 wt. %, preferably 0.05 to 5 wt. % with respect to the total amount of ε-caprolactone and the polymerization initiator.

Polymerization Initiator

In the present invention, a known polymerization initiator can be employed in the ring-opening polymerization of ε-caprolactone. Examples of such polymerization initiator include monools such as methanol, ethanol, 1-propanol, 2-propanol, butanols or phenol, diols such as ethylene glycol, 1,3-propanediol, 1,4-butanediol, diethylene glycol, 1,5-pentanediol, 1,6-hexanediol, 1,7-heptanediol, 1,8-octanediol or 1,10-decanediol, triols such as glycerin or trimethylol propane, and polyols such as neopentyl glycol or pentaerythritol. Such initiator may be employed singly or as a mixture of at least two initiators.

The molar ratio of the polymerization initiator to be employed in the present invention and ε-caprolactone can be suitably selected according to the polymerization ratio of the desired aliphatic polyester, and is normally within a range of 1:1 to 1:5,000, preferably within a range of 1:1 to 1:2,000.

The ring-opening polymerization of ε-caprolactone can be executed by a polymerization reaction of ε-caprolactone in the presence of the polymerization catalyst and the polymerization initiator under the presence of inert gas or under a reduced pressure. The ring-opening polymerization of ε-caprolactone is preferably executed in a nitrogen atmosphere for the ease of operation.

In the ring-opening polymerization of ε-caprolactone, the reaction temperature and time can be arbitrarily selected. The reaction temperature is preferably equal to 50° C. or higher, particularly 100° C. or higher in order to obtain a sufficiently high reaction speed, and is preferably not exceeding 200° C., particularly not exceeding 180° C. in order to substantially avoid coloration of aliphatic polyester by oxidation or decomposition of the generated aliphatic polyester. Also the reaction time can be arbitrarily selected within a range not affecting the quality of the generated aliphatic polyester.

The ring-opening polymerization of ε-caprolactone can also be executed in a solvent. The solvent is preferably an inactive solvent not reacting with ε-caprolactone, polymerization catalyst or polymerization initiator, selected from aromatic hydrocarbons such as toluene or xylene, or aliphatic or alicyclic hydrocarbons such as hexane or cyclohexane. Preferably such solvent is substantially anhydrous.

The weight-average molecular weight of aliphatic polyester obtained by the ring-opening polymerization of ε-caprolactone is preferably 1,000 or higher, particularly 30,000 or higher in terms of polystyrene and preferably 1,000,000 or lower, particularly 500,000 or lower in terms of polystyrene.

The aliphatic polyester of the present invention thus obtained can be utilized in various industrial fields by modifying the weight-average molecular weight or the functional group contained therein. For example, the aliphatic polyester of a weight-average molecular weight of 1,000 to 5,000 utilizing glycol as a polymerization initiator is extremely useful, exploiting the presence of a hydroxyl group therein, as a raw material for polyurethane or paints. Also the aliphatic polyester having a weight-average molecular weight exceeding 50,000 has a practical mechanical strength and is usable in plastic molded articles, films or hot-melt adhesives. The molding can be executed, for example, by compression molding, injection molding, extrusion molding, mold casting or transfer molding utilizing a mold.

Also the aliphatic polyester of the present invention may be mixed, within a range not affecting the object of the present invention, with another resinous component, a rubber component, a heat resistance stabilizer, a flame retarding agent, a slipping agent, an antiblocking agent, an anticlouding agent, a friction reducing agent, a filler, a dye, a pigment, natural oil, synthetic oil or wax. The mixing ratio is not particularly limited and can be suitably determined.

In the following, the present invention will be further clarified by way of examples, but the present invention is by no means limited to such examples.

EXAMPLE 1

500 parts by weight of starch (supplied by Wako Pure Chemical Industries Co.) were put into 4,500 parts by weight of water and were dissolved under heating. Then 5,000 parts by weight of 3 mol/l sulfuric acid were added and reacted under agitation for 5 hours at 80° C. After the reaction, the aqueous solution was neutralized by the addition of anhydrous sodium carbonate, then was passed through a column of the ion exchange resin (Amberlite IR-120B, supplied by Organo Co.) and the solvent was distilled off. Then the reaction mixture was separated and purified to obtain 300 parts by weight of glucose.

The $^{13}$C-NMR (100 MHz, internal standard material: TMS (tetramethylsilane), DMSO-$d_6$) of the synthesized glucose was measured with FT-NMR DPX400 (manufactured by Bruker Inc.) to obtain chemical shifts δ (ppm) as follows:

α-type: 92.12, 73.04, 72.29, 71.80, 70.58, 61.20; and
β-type: 96.79, 76.70, 76.59, 74.78, 70.30, 61.00.

8,000 parts by weight of 12% aqueous solution of barium carbonate were saturated with carbon dioxide, and 330 parts by weight of bromine and 300 parts by weight of the glucose were added and agitated for 30 minutes at 25° C. to obtain 250 parts by weight of gluconolactone represented by the following chemical formula (III):

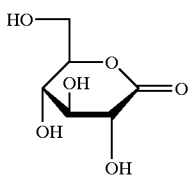

(III)

The $^{13}$C-NMR of the synthesized gluconolactone was measured to obtain chemical shifts δ (ppm) as follows:

gluconolactone: $^{13}$C-NMR (100 MHz, TMS, DMSO-d$_6$) δ (ppm): 171.88, 81.23, 73.79, 71.43, 67.82, 60.14.

87 parts by weight of red phosphorus and 250 parts by weight of the gluconolactone were added to 12,000 parts by weight of hydroiodic acid (55 mass %), and were refluxed for 20 hours at 130° C. The reaction mixture was filtered, then the filtrate was extracted with ether and the extract was washed with 5% aqueous solution of sodium hydrosulfite. After the solvent ether was distilled off, distillation under a reduced pressure was executed to obtain 147 parts by weight of caproic acid.

The $^{13}$C-NMR of the synthesized caproic acid was measured to obtain chemical shifts δ (ppm) as follows:

caproic acid: $^{13}$C-NMR (100 MHz, TMS, CDCl$_3$) δ (ppm): 180.78, 34.24, 31.36, 24.49, 22.42, 13.90.

147 parts by weight of the caproic acid were added to 1,000 parts by weight of 90% sulfuric acid saturated with chlorine and were reacted for 6 hours at 25° C. to obtain 95 parts by weight of 6-chlorocaproic acid.

The $^{13}$C-NMR of the synthesized 6-chlorocaproic acid was measured to obtain chemical shifts δ (ppm) as follows:

6-chlorocaproic acid: $^{13}$C-NMR (100 MHz, TMS, CDCl$_3$) δ (ppm): 180.18, 44.69, 33.93, 32.25, 26.36, 23.98.

95 parts by weight of the 6-chlorocaproic acid were boiled with an aqueous solution of the equivalent amount of sodium hydroxide to obtain 69 parts by weight of ε-caprolactone.

The $^{13}$C-NMR of the synthesized ε-caprolactone was measured to obtain chemical shifts δ (ppm) as follows:

ε-caprolactone: $^{13}$C-NMR (100 MHz, TMS, CDCl$_3$) δ (ppm): 176.23, 69.30, 34.56, 29.35, 28.93, 22.98.

69 parts by weight of the ε-caprolactone were heated to 155° C. in a nitrogen atmosphere, and 0.21 parts by weight of tri-iso-propoxy-aluminum as a polymerization catalyst and 0.41 parts by weight of diethylene glycol as a polymerization initiator were added to execute ring-opening polymerization thereby obtaining aliphatic polyester. The polymerization time was 10 hours. The obtained aliphatic polyester shows a weight-average molecular weight of 300,000 in terms of polystyrene and an average degree of polymerization of 2,630.

The $^1$H-NMR and $^{13}$C-NMR of the synthesized aliphatic polyester were measured to obtain chemical shifts δ (ppm) as follows:

aliphatic polyester: $^1$H-NMR (400 MHz, TMS, CDCl$_3$) δ (ppm): 1.36 to 1.42 (2H, m), 1.61 to 1.69 (4H, m), 2.31 (2H, t), 4.06 (2H, t); and aliphatic polyester: $^{13}$C-NMR (100 MHz, TMS, CDCl$_3$) δ (ppm): 24.59, 25.54, 28.36, 34.12, 64.16, 173.56.

These results of measurement confirmed that the desired aliphatic polyester was synthesized.

EXAMPLE 2

300 parts by weight of glucose, obtained in the same manner as in the example 1, were oxidized and hydrolyzed in 2,500 parts by weight of 27N sulfuric acid saturated with bromine to obtain 290 parts by weight of gluconic acid represented by the following chemical formula (IV):

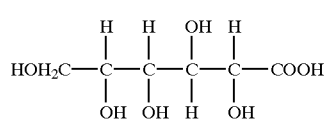

(IV)

100 parts by weight of red phosphorus and 290 parts by weight of the gluconic acid were added to 14,000 parts by weight of hydroiodic acid (55 mass %) and were refluxed for 20 hours at 130° C. Then the subsequent process was conducted in the same manner as in the example 1 to obtain 155 parts by weight of caproic acid.

155 parts by weight of the caproic acid were added to 1,000 parts by weight of 90% sulfuric acid saturated with chlorine and were reacted for 6 hours at 25° C. to obtain 100 parts by weight of 6-chlorocaproic acid.

100 parts by weight of the 6-chlorocaproic acid were boiled with an aqueous solution of the equivalent amount of sodium hydroxide to obtain 73 parts by weight of ε-caprolactone.

73 parts by weight of ε-caprolactone were heated to 160° C. in a nitrogen atmosphere, and 0.22 parts by weight of di-iso-propyl zinc as a polymerization catalyst and 0.44 parts by weight of 1,4-butanediol as a polymerization initiator were added to execute ring-opening polymerization thereby obtaining aliphatic polyester. The polymerization time was 10 hours. The obtained aliphatic polyester showed a weight-average molecular weight of 250,000 in terms of polystyrene and an average degree of polymerization of 2,190.

The measurement of $^1$H-NMR and $^{13}$C-NMR provided spectra similar to those in the example 1, confirming that the desired aliphatic polyester was synthesized.

Evaluation of Physical Properties

The aliphatic polyesters synthesized in the examples 1 and 2 were subjected to evaluation of various physical properties, of which results are shown in Table 1. Also as a reference example 1, Celgreen (polycaprolactone plastic P-H7 manufactured by Daicel Chemical Industries, Co.) was included in the comparative evaluation.

TABLE 1

|  | Example 1 | Example 2 | Reference Example 1 |
|---|---|---|---|
| Tensile yield strength (JIS) K7113 Pa | 0.25 | 0.22 | 0.20 |
| Tensile modulus (JIS) K7113 Pa | 2.45 | 2.30 | 2.25 |

TABLE 1-continued

|  | Example 1 | Example 2 | Reference Example 1 |
|---|---|---|---|
| Bending strength (JIS) K7203 Pa | 0.43 | 0.40 | 0.37 |
| Bending modulus (JIS) K7203 Pa | 5.00 | 4.75 | 4.41 |

These results indicate that the aliphatic polyesters synthesized in the examples 1 and 2 have physical properties equivalent or superior to those of the aliphatic polyester P-H7 of Daicel Chemical of the reference example 1 excellent in the strength and elongation, and can be satisfactorily used as a substitute for the conventionally known plastics derived from petroleum.

As explained in the foregoing, the present invention enables to produce aliphatic polyester by the ring-opening polymerization of ε-caprolactone obtained from starch via glucose, and such aliphatic polyester has sufficient physical properties such as mechanical strength and can be utilized for plastic molded products. Furthermore, this fact opens up a way of obtaining high-quality plastic materials from starch instead of petroleum, thereby establishing starch as an efficient resource.

In the following, the present invention will be clarified further by another embodiment.

More specifically, the method of the present invention for producing aliphatic polyester in another embodiment comprises the steps of:

(i) hydrolyzing cellulose to obtain glucose;
(ii) oxidizing the glucose to obtain gluconolactone or gluconic acid;
(iii) reducing the gluconolactone or the gluconic acid to obtain caproic acid;
(iv) chlorinating the caproic acid to obtain 6-chlorocaproic acid;
(v) cyclizing the 6-chlorocaproic acid to obtain ε-caprolactone; and
(vi) executing ring-opening polymerization of the ε-caprolactone to obtain aliphatic polyester.

As the raw material cellulose in preparing glucose from cellulose, there can naturally be employed not only commercially available cellulose but also recycled cellulose obtained by suitably processing waste paper or wood materials such as waste timbers. Therefore the method of the present invention for synthesizing aliphatic polyester from cellulose opens up a novel way of re-utilizing recycled cellulose as a resource.

In the following there will be explained each of the aforementioned steps (i) to (vi).

Step (i) (Cellulose to Glucose)

Conversion from cellulose to glucose can be achieved for example by decomposition with an enzyme such as cellulase, decomposition with an acid such as sulfuric acid or hydrochloric acid or decomposition with ultracritical water, among which decomposition with an enzyme such as cellulase, namely hydrolysis with an enzyme, is preferred because of simplicity in operation.

Step (ii) (Glucose to Gluconolactone or Gluconic Acid)

Conversion from glucose to gluconolactone can be achieved for example by bromine oxidation of glucose or by a method utilizing notatin which is a glucose oxidase. Among these, the bromine oxidation is preferred in consideration of the yield.

Conversion from glucose to gluconic acid can be achieved for example by oxidizing and hydrolyzing glucose in sulfuric acid saturated with bromine, or by electrolytic oxidation of a glucose solution or by fermentation of gluconic acid utilizing bacteria of Penicillium family. Among these, the method of oxidizing and hydrolyzing glucose in concentrated sulfuric acid saturated with bromine, namely oxidation utilizing bromine and concentrated sulfuric acid, is preferred in consideration of the yield.

In the present specification, concentrated sulfuric acid means sulfuric acid of 27N.

Step (iii) (Gluconolactone or Gluconic Acid to Caproic Acid)

Conversion of gluconolactone or gluconic acid to caproic acid can be achieved for example by reduction thereof with hydroiodic acid and red phosphorus. In this reaction, it is desirable that the hydroxyl group alone of gluconolactone or gluconic acid is oxidized.

The amount of red phosphorus employed in the reduction is preferably 1.8 to 2.4 equivalents with respect to gluconolactone or gluconic acid. Hydroiodic acid employed in the reduction preferably has a concentration of 50 to 60 mass %, and is preferably employed in a weight of 40 to 60 times with respect to the weight of gluconolactone or gluconic acid. The reducing reaction is completed by refluxing gluconolactone or gluconic acid and red phosphorus in hydroiodic acid for about 20 hours.

Step (iv) (Caproic Acid to 6-Chlorocaproic Acid)

Conversion from caproic acid to 6-chlorocaproic acid can be achieved for example by chlorination conducted by reacting caproic acid with chlorine in concentrated sulfuric acid.

Step (v) (6-Chlorocaproic Acid to ε-Caprolactone)

Conversion from 6-chlorocaproic acid to ε-caprolactone can be achieved for example by cyclization by boiling 6-chlorocaproic acid in an aqueous solution of sodium hydroxide.

Step (vi) (ε-Caprolactone to Aliphatic Polyester)

Conversion from ε-caprolactone to aliphatic polyester can be achieved for example by ring-opening polymerization utilizing a polymerization catalyst and a polymerization initiator.

In the following, the another embodiment of the present invention will be further clarified by way of examples, but the present invention is by no means limited to such examples. Also the description same as that in the foregoing embodiment will be omitted for the purpose of simplicity.

EXAMPLE 3

500 parts by mass of cellulose (KC Flock W-100; supplied by Nippon Paper Co.) were put into 15,050 parts by mass of an enzyme solution and agitated for 8 hours at 45° C. The enzyme solution was prepared by dissolving 50 parts by mass of cellulase (Meicellase TP60; supplied by Meiji Seika Co.) in 15,000 parts by mass of an aqueous solution of acetic acid/sodium acetate (pH 4.5). After the reaction, 1,000 parts by mass of methanol were added, then the water-soluble residue was filtered off and the solution was passed through a column of the ion exchange resin (Amberlite IR-120B, supplied by Organo Co.) and the solvent was distilled off. Then the reaction mixture was separated and purified to obtain 300 parts by mass of glucose.

8,000 parts by mass of a 12% aqueous solution of barium carbonate were saturated with carbon dioxide, and 330 parts by mass of bromine and 300 parts by mass of the glucose were added and agitated for 30 minutes at 25° C. to obtain 250 parts by mass of gluconolactone represented by the following chemical formula (III):

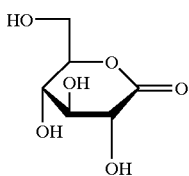

(III)

87 parts by mass of red phosphorus and 250 parts by mass of the gluconolactone were added to 10,500 parts by mass of hydroiodic acid (55 mass %), and were refluxed for 20 hours. The reaction mixture was filtered, then the filtrate was extracted with ether and the extract was washed with a 5% aqueous solution of sodium hydrosulfite. After the solvent ether was distilled off, distillation under a reduced pressure was executed to obtain 147 parts by mass of caproic acid.

147 parts by mass of the caproic acid were added to 1,000 parts by mass of 27N sulfuric acid saturated with chlorine and were reacted for 6 hours at 25° C. to obtain 95 parts by mass of 6-chlorocaproic acid.

95 parts by mass of the 6-chlorocaproic acid were boiled with an aqueous solution of the equivalent amount of sodium hydroxide to obtain 69 parts by mass of ε-caprolactone.

69 parts by mass of the ε-caprolactone were heated to 155° C. in a nitrogen atmosphere, and 0.21 parts by mass of tri-iso-propoxy-aluminum and 0.41 parts by mass of diethylene glycol were added to execute ring-opening polymerization thereby obtaining aliphatic polyester. The polymerization time was 10 hours, and the obtained aliphatic polyester showed a weight-average molecular weight of 300,000.

The $^1$H-NMR and $^{13}$C-NMR of the synthesized aliphatic polyester were measured with FT-NMR DPX400 (Bruker) as follows:

$^1$H-NMR (400 MHz, TMS, CDCl$_3$) δ (ppm): 1.36 to 1.42 (2H, m), 1.61 to 1.69 (4H, m), 2.31 (2H, t), 4.06 (2H, t); and $^{13}$C-NMR (100 MHz, TMS, CDCl$_3$) δ (ppm): 24.59, 25.54, 28.36, 34.12, 64.16, 173.56.

These results of measurement confirmed that the desired aliphatic polyester was synthesized.

EXAMPLE 4

300 parts by mass of glucose, obtained in the same manner as in the example 3, were oxidized and hydrolyzed in 2,500 parts by mass of 27N sulfuric acid saturated with bromine to obtain 290 parts by mass of gluconic acid represented by the following chemical formula (IV):

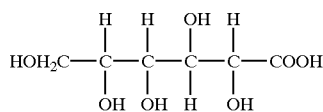

(IV)

100 parts by mass of red phosphorus and 290 parts by mass of the gluconic acid were added to 16,300 parts by mass of hydroiodic acid (55 mass %) and were refluxed for 20 hours. Then the subsequent process was conducted in the same manner as in the example 3 to obtain 155 parts by mass of caproic acid.

155 parts by mass of the caproic acid were added to 1,000 parts by mass of 27N sulfuric acid saturated with chlorine and were reacted for 6 hours at 25° C. to obtain 100 parts by mass of 6-chlorocaproic acid.

100 parts by mass of the 6-chlorocaproic acid were boiled with an aqueous solution of the equivalent amount of sodium hydroxide to obtain 73 parts by mass of ε-caprolactone.

73 parts by mass of ε-caprolactone were heated to 160° C. in a nitrogen atmosphere, and 0.22 parts by mass of di-iso-propyl zinc and 0.44 parts by mass of 1,4-butanediol were added to execute ring-opening polymerization thereby obtaining aliphatic polyester. The polymerization time was 10 hours, and the obtained aliphatic polyester showed a weight-average molecular weight of 250,000.

The measurement of $^1$H-NMR provided spectra similar to those in the example 3, confirming that the desired aliphatic polyester was synthesized.

EXAMPLE 5

Recycled paper for PPC (EN-500, A4: Canon Sales Co.), after use (copied on one side in a copying apparatus), was cut into 5 mm squares, and 500 parts by mass of such cut paper were put into 15,050 parts by mass of an enzyme solution and agitated for 10 hours at 45° C. The enzyme solution was prepared by dissolving 50 parts by mass of cellulase (Meicellase TP60; supplied by Meiji Seika Co.) in 15,000 parts by mass of an aqueous solution of acetic acid/sodium acetate (pH 4.5). After the reaction, 1,000 parts by mass of methanol were added, then the water-soluble residue was filtered off and the solution was passed through a column of the ion exchange resin (Amberlite IR-120B, supplied by Organo Co.) and the solvent was distilled off. Then the reaction mixture was separated and purified to obtain 280 parts by mass of glucose.

7,500 parts by mass of a 12% aqueous solution of barium carbonate were saturated with carbon dioxide, and 300 parts by mass of bromine and 280 parts by mass of the glucose were added and agitated for 30 minutes at 25° C. to obtain 230 parts by mass of gluconolactone.

80 parts by mass of red phosphorus and 230 parts by mass of the gluconolactone were added to 13,000 parts by mass of hydroiodic acid (55 mass %), and were refluxed for 20 hours. The reaction mixture was filtered. Thereafter the process was executed in the same manner as in the example 3 to obtain 135 parts by mass of caproic acid.

135 parts by mass of the caproic acid were added to 1,000 parts by mass of 27N sulfuric acid saturated with chlorine and were reacted for 6 hours at 25° C. to obtain 87 parts by mass of 6-chlorocaproic acid.

87 parts by mass of the 6-chlorocaproic acid were boiled with an aqueous solution of the equivalent amount of sodium hydroxide to obtain 63 parts by mass of ε-caprolactone.

63 parts by mass of the ε-caprolactone were heated to 150° C. in a nitrogen atmosphere, and 0.19 parts by mass of tetra-n-butoxy-titanium and 0.38 parts by mass of 1,8-octane-diol were added to execute ring-opening polymerization thereby obtaining aliphatic polyester. The polymerization time was 10 hours, and the obtained aliphatic polyester showed a weight-average molecular weight of 280,000.

The measurement of $^1$H-NMR provided spectra similar to those in the example 3, thus confirming that the desired aliphatic polyester was synthesized.

EXAMPLE 6

280 parts by mass of glucose, obtained in the same manner as in the example 5, were oxidized and hydrolyzed in 2,300 parts by mass of 27N sulfuric acid saturated with bromine to obtain 270 parts by mass of gluconic acid.

95 parts by mass of red phosphorus and 270 parts by mass of the gluconic acid were added to 12,200 parts by mass of hydrolodic acid (55 mass %) and were refluxed for 20 hours. Then the subsequent process was conducted in the same manner as in the example 3 to obtain 144 parts by mass of caproic acid.

144 parts by mass of the caproic acid were added to 1,000 parts by mass of 27N sulfuric acid saturated with chlorine and were reacted for 6 hours at 25° C. to obtain 93 parts by mass of 6-chlorocaproic acid.

93 parts by mass of the 6-chlorocaproic acid were boiled with an aqueous solution of the equivalent amount of sodium hydroxide to obtain 68 parts by mass of ε-caprolactone.

68 parts by mass of ε-caprolactone were heated to 155° C. in a nitrogen atmosphere, and 0.20 parts by mass of tetra-t-butoxy-zirconium and 0.40 parts by mass of methanol were added to execute ring-opening polymerization thereby obtaining aliphatic polyester. The polymerization time was 9 hours, and the obtained aliphatic polyester showed a weight-average molecular weight of 210,000.

The measurement of $^1$H-NMR provided spectra similar to those in the example 3, confirming that the desired aliphatic polyester was synthesized.

Evaluation of Physical Properties

The aliphatic polyesters synthesized in the examples 3 to 6 were subjected to evaluation of various physical properties, of which results are shown in Table 2. Also as a reference example 2, Celgreen (polycaprolactone plastic P-H7 manufactured by Daicel Chemical Industries, Co.) was included in the comparative evaluation.

TABLE 2

| | Example 3 | Example 4 | Example 5 | Example 6 | Reference Example 2 |
|---|---|---|---|---|---|
| Tensile yield strength (JIS) K7113 Pa | 0.25 | 0.22 | 0.23 | 0.21 | 0.20 |
| Tensile modulus (JIS) K7113 Pa | 2.45 | 2.30 | 2.40 | 2.27 | 2.25 |
| Bending strength (JIS) K7203 Pa | 0.43 | 0.40 | 0.42 | 0.38 | 0.37 |
| Bending modulus (JIS) K7203 Pa | 5.00 | 4.75 | 4.85 | 4.60 | 4.41 |

These results indicate that the aliphatic polyesters synthesized in the examples 3 to 6 have physical properties equivalent or superior to those of the aliphatic polyester P-H7 of Daicel Chemical of the reference example 2 which is excellent in the strength and elongation, and can therefore be satisfactorily used as a substitute for the conventionally known plastics derived from petroleum.

As explained in the foregoing, the present invention enables to produce aliphatic polyester by the ring-opening polymerization of ε-caprolactone obtained from cellulose via glucose, and such aliphatic polyester has sufficient physical properties such as mechanical strength and can be utilized for plastic molded products. Furthermore, there is provided an efficient way of recycling cellulose as a resource.

In the following there will be explained another embodiment of the present invention.

In the present embodiment, gluconolactone is efficiently converted into caproic acid with such a high purity usable as a monomer for aliphatic polyester. Also gluconic acid is efficiently converted into caproic acid with such a high purity usable as a monomer for aliphatic polyester. As a result, it is rendered possible to produce aliphatic polyester utilizing caproic acid obtained from starch via glucose, namely to obtain plastics of high quality employing starch as the starting material. It is thus possible to produce aliphatic polyester from waste starch as the raw material, thereby recycling starch as a resource.

In the following there will be explained each of the steps.

Starch to Glucose

Conversion from starch to glucose can be achieved for example by hydrolysis with a dilute acid such as sulfuric acid, hydrolysis with an enzyme such as amylase or maltase, or hydrolysis with ultracritical water.

Glucose to Gluconolactone or Gluconic Acid

Conversion from glucose to gluconolactone can be achieved for example by bromine oxidation of glucose or by a method utilizing notatin which is a glucose oxidase.

Conversion from glucose to gluconic acid can be achieved for example by oxidizing and hydrolyzing glucose in sulfuric acid saturated with bromine, or by electrolytic oxidation of a glucose solution or by gluconic acid fermentation utilizing bacteria of Penicillium family.

Gluconolactone or Gluconic Acid to Caproic Acid

The conversion step from gluconolactone or gluconic acid to caproic acid is an important step in the present invention, and is preferably executed by reduction with hydroiodic acid and red phosphorus, from the standpoint of the yield and the selectivity. In this reaction, the hydroxyl group alone of gluconolactone or gluconic acid is substantially oxidized.

The reaction condition of this step is carefully selected in consideration of the yield and the purity of the caproic acid to be obtained.

More specifically, the amount of red phosphorus employed in the reduction is preferably 1.5 molar equivalents or larger with respect to gluconolactone or gluconic acid, more preferably 1.7 molar equivalents or larger and most preferably 1.8 molar equivalents or larger. On the other hand, from the standpoint of suppressing by-products, it is preferably 3.0 molar equivalents or less, more preferably 2.7 molar equivalents or less and most preferably 2.4 molar equivalents or less.

Hydroiodic acid employed in the reduction preferably has a concentration of 50 to 60 mass %, and is preferably employed in a mass amount of 30 times or larger with respect to the mass of gluconolactone or gluconic acid, more preferably 35 times or larger and most preferably 40 times or larger. On the other hand, from the standpoint of suppressing by-products, it is preferably 70 times in mass or less, more preferably 65 times or less and most preferably 60 times or less.

A mixture containing gluconolactone or gluconic acid, red phosphorus and hydroiodic acid is heated to a refluxing state, which is maintained until the completion of the reduction reaction. The refluxing time is preferably 10 hours or longer from the standpoint of securing a sufficient yield, more preferably 13 hours or longer and most preferably 15 hours or longer. On the other hand, from the standpoint of suppressing by-products, it is preferably 30 hours or shorter, more preferably 27 hours or shorter and most preferably 25 hours or shorter.

Caproic Acid to 5-Chlorocaproic Acid

Conversion from caproic acid to 5-chlorocaproic acid can be achieved for example by chlorination by reacting caproic acid with N-chloro-diisopropylamine in concentrated sulfuric acid. This reaction is described by N. C. Deno et al., J. Am. Chem. Soc., 93, 438–440 (1971).

5-Chlorocaproic Acid to δ-Caprolactone

Conversion from 5-chlorocaproic acid to δ-caprolactone represented by the following chemical formula (V) can be achieved for example by boiling 5-chlorocaproic acid in an aqueous solution of sodium hydroxide:

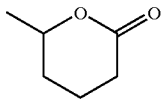

(V)

(δ-caprolactone to aliphatic polyester; ring-opening polymerization)

In the present invention, a known ring-opening polymerization catalyst can be employed as the polymerization catalyst in the ring-opening polymerization of δ-caprolactone. Examples of such catalyst include tin dichloride, tin tetrachloride, tetra-n-butoxy-germanium, tetramethoxy-germanium, tetraethoxy-germanium, triethoxy-aluminum, tri-n-propoxy-aluminum, tri-iso-propoxy-aluminum, tri-n-butoxy-aluminum, tri-iso-butoxy-aluminum, aluminum chloride, triethyl-aluminum, trimethyl-aluminum, di-iso-propyl zinc, dimethyl-zinc, diethyl-zinc, zinc chloride, tetra-n-propoxy-titanium, tetra-n-butoxy-titanium, tetra-t-butoxy-titanium, tetraethoxy-zirconium, tetramethoxy-zirconium, tetra-iso-propoxy-zirconium, tetra-n-butoxy-zirconium, tetra-iso-butoxy-zirconium, tetra-t-butoxy-zirconium, and organic compounds of rare earth metals such as La, Nd, Sm, Er, Tm, Yb or Lu. Such catalyst may be employed singly or a mixture of at least two catalysts.

The amount of polymerization catalyst is usually within a range of 0.01 to 10 mass %, preferably 0.05 to 5 mass % with respect to the total amount of δ-caprolactone and the polymerization initiator.

In the present invention, a known polymerization initiator can be employed in the ring-opening polymerization of δ-caprolactone. Examples of such polymerization initiator include monools such as methanol, ethanol, 1-propanol, 2-propanol, butanols or phenol, diols such as ethylene glycol, 1,3-propanediol, 1,4-butanediol, diethylene glycol, 1,5-pentanediol, 1,6-hexanediol, 1,7-heptanediol, 1,8-octanediol or 1,10-decanediol, triols such as glycerin or trimethylol propane, and polyols such as neopentyl glycol or pentaerythritol. Such initiator may be employed singly or as a mixture of at least two initiators.

The molar ratio of the polymerization initiator to be employed in the present invention and δ-caprolactone can be suitably selected according to the polymerization ratio of the desired aliphatic polyester, and is normally within a range of 1:1 to 1:5,000, preferably within a range of 1:1 to 1:2,000.

The ring-opening polymerization of δ-caprolactone can be executed by a polymerization reaction of δ-caprolactone in the presence of the polymerization catalyst and the polymerization initiator under the presence of inert gas or under a reduced pressure. The ring-opening polymerization of δ-caprolactone is preferably executed in a nitrogen atmosphere for the ease of operation.

In the ring-opening polymerization of δ-caprolactone, the reaction temperature and time can be arbitrarily selected. The reaction temperature is preferably within a range of 50 to 200° C., more preferably 100 to 180° C. The reaction is sufficiently fast at a reaction temperature of 50° C. or higher. Also the coloration of aliphatic polyester by oxidation reaction or the decomposition of the generated aliphatic polyester can be suppressed at a reaction temperature not exceeding 200° C. Also the reaction time can be arbitrarily selected within a range not affecting the quality of the generated aliphatic polyester.

The ring-opening polymerization of δ-caprolactone can also be executed in a solvent. The solvent is preferably an inactive solvent not reacting with δ-caprolactone, polymerization catalyst or polymerization initiator, preferably selected from aromatic hydrocarbons such as toluene or xylene, or aliphatic or alicyclic hydrocarbons such as hexane or cyclohexane. Preferably such solvent is substantially anhydrous.

The weight-average molecular weight of aliphatic polyester obtained by the ring-opening polymerization of δ-caprolactone is preferably within a range of 1,000 to 1,000,000, preferably 30,000 to 500,000 in terms of standard polystyrene.

The aliphatic polyesters thus obtained can be utilized as plastic materials replacing those conventionally employed in various fields, and can be applied to various industrial field by modifying the weight-average molecular weight or the functional group contained therein. For example, the aliphatic polyester of a weight-average molecular weight of 1,000 to 5,000 utilizing glycol as the polymerization initiator is extremely useful, exploiting the presence of a hydroxyl group therein, as a raw material for polyurethane or paints. Also the aliphatic polyester having a weight-average molecular eight exceeding 50,000 has a practical mechanical strength and is usable in plastic molded articles, films or hot-melt adhesives.

In the following, the another embodiment of the present invention will be further clarified by way of examples, but the present invention is by no means limited to such examples. Also the used reagents are commercially available ones of high purity, unless otherwise specified.

EXAMPLE 7

500 parts by mass of starch (supplied by Wako Pure Chemical Industries Co.) were put into 4,500 parts by mass of water and were dissolved under heating. Then 5,000 parts by mass of 3 mol/l sulfuric acid were added and reacted under agitation for 5 hours at 80° C. After the reaction, the aqueous solution was neutralized by the addition of anhydrous sodium carbonate, then was passed through a column of the ion exchange resin (Amberlite IR-120B, supplied by Organo Co.) and the solvent was distilled off. Then the reaction mixture was separated and purified to obtain 300 parts by mass of glucose.

The $^{13}$C-NMR (100 MHz, DMSO-$d_6$) of the synthesized glucose was measured with FT-NMR DPX400 (manufactured by Bruker Inc.). As a result, there were confirmed the following peak δ values resulting from α-type glucose: 92.12 ppm, 73.04 ppm, 72.29 ppm, 71.80 ppm, 70.58 ppm and 61.20 ppm; and those resulting from δ-type glucose: 96.79 ppm, 76.70 ppm, 76.59 ppm, 74.78 ppm, 70.30 ppm and 61.00 ppm.

8,000 parts by mass of a 12% aqueous solution of barium carbonate were saturated with carbon dioxide, and 330 parts by mass of bromine and 300 parts by mass of the glucose were added and agitated for 30 minutes at 25° C. to obtain 250 parts by mass of gluconolactone represented by the following chemical formula (III):

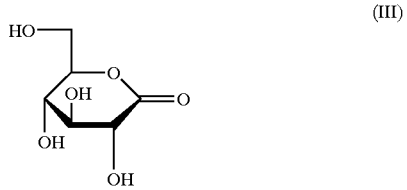

(III)

The $^{13}$C-NMR (100 MHz, DMSO-d$_6$) of the synthesized gluconolactone was measured to obtain the following δ values: 171.88 ppm, 81.23 ppm, 73.79 ppm, 71.43 ppm, 67.82 ppm and 60.14 ppm.

87 parts by mass of red phosphorus and 250 parts by mass of the gluconolactone were added to 12,000 parts by mass of hydroiodic acid (55 mass %), and were refluxed for 20 hours. The reaction mixture was filtered, then the filtrate was extracted with ether and the extract was washed with a 5% aqueous solution of sodium hydrosulfite. After the solvent ether was distilled off, distillation under a reduced pressure was executed to obtain 147 parts by mass of caproic acid.

147 parts by mass of the obtained caproic acid and an equivalent amount of N-chlorodiisopropylamine were added to 1,000 parts by mass of 84% sulfuric acid and were reacted for 5 hours at 25° C. to obtain 177 parts by mass of 5-chlorocaproic acid. Then 177 parts by mass of the 5-chlorocaproic acid were boiled with an aqueous solution of an equivalent amount of sodium hydroxide to obtain 129 parts by mass of δ-caprolactone. The $^{13}$C-NMR (100 MHz, TMS, CDCl$_3$) of the synthesized δ-caprolactone was measured to obtain the following δ values: 19.90 ppm, 20.88 ppm, 34.27 ppm, 35.31 ppm, 70.44 ppm and 172.84 ppm.

129 parts by mass of the δ-caprolactone were heated to 155° C. in a nitrogen atmosphere, and 0.39 parts by mass of tri-iso-propoxy-aluminum and 0.77 parts by mass of diethylene glycol were added to execute ring-opening polymerization thereby obtaining aliphatic polyester. The polymerization time was 10 hours, and the obtained aliphatic polyester showed a weight-average molecular weight of 290,000.

The $^{13}$C-NMR (100 MHz, TMS, CDCl$_3$) of the synthesized aliphatic polyester was measured to obtain the following δ values: 19.95 ppm, 20.82 ppm, 34.46 ppm, 35.26 ppm, 70.31 ppm and 173.37 ppm, thereby confirming that the desired aliphatic polyester was synthesized.

EXAMPLE 8

300 parts by mass of glucose, obtained in the same manner as in the example 7, were oxidized and hydrolyzed in 2,500 parts by mass of 13.5 mol/l sulfuric acid saturated with bromine to obtain 290 parts by mass of gluconic acid represented by the following chemical formula (IV):

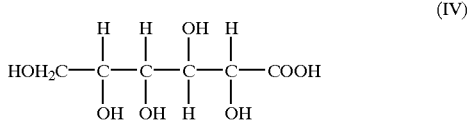

(IV)

100 parts by mass of red phosphorus and 290 parts by mass of the obtained gluconic acid were added to 14,000 parts by mass of hydroiodic acid (55 mass %) and were refluxed for 20 hours. Then the subsequent process was conducted in the same manner as in the example 7 to obtain 155 parts by mass of caproic acid.

155 parts by mass of the caproic acid and an equivalent amount of N-chlorodiisopropylamine were added to 1,000 parts by mass of 84% sulfuric acid and were reacted for 6 hours at 25° C. to obtain 187 parts by mass of 5-chlorocaproic acid. 187 parts by mass of the 5-chlorocaproic acid were boiled with an aqueous solution of an equivalent amount of sodium hydroxide to obtain 136 parts by mass of δ-caprolactone.

136 parts by mass of δ-caprolactone were heated to 160° C. in a nitrogen atmosphere, and 0.41 parts by mass of di-iso-propyl zinc and 0.82 parts by mass of 1,4-butanediol were added to execute ring-opening polymerization thereby obtaining aliphatic polyester. The polymerization time was 10 hours, and the obtained aliphatic polyester showed a weight-average molecular weight of 220,000.

The measurement of $^{13}$C-NMR provided spectra similar to those in the example 7, confirming that the desired aliphatic polyester was synthesized.

Evaluation of Physical Properties

The aliphatic polyesters synthesized in the examples 7 and 8 were subjected to evaluation of various physical properties, of which results are shown in Table 3. Also as a reference example 3, Celgreen (polycaprolactone plastic P-H7 manufactured by Daicel Chemical Industries, Co.) was included in the comparative evaluation.

TABLE 3

| | Example 7 | Example 8 | Reference Example 3 |
|---|---|---|---|
| Tensile yield strength (JIS) K7113 Pa | 0.30 | 0.26 | 0.20 |
| Tensile modulus (JIS) K7113 Pa | 2.50 | 2.40 | 2.25 |
| Bending strength (JIS) K7203 Pa | 0.50 | 0.45 | 0.37 |
| Bending modulus (JIS) K7203 Pa | 5.10 | 4.86 | 4.41 |

These results indicate that the aliphatic polyesters synthesized in the examples 7 and 8 have physical properties equivalent or superior to those of the aliphatic polyester P-H7 of Daicel Chemical of the reference example 3 which is excellent in the strength and elongation, and can be satisfactorily used as a substitute for the conventionally known plastics.

As explained in the foregoing, the present invention enables to produce aliphatic polyester by the ring-opening polymerization of δ-caprolactone obtained from starch via glucose, and such aliphatic polyester has sufficient physical properties such as mechanical strength and can be utilized for plastic molded products. Furthermore, this fact opens up a way of obtaining high-quality plastic materials from starch instead of petroleum, thereby establishing starch as an efficient resource.

In the following, aforementioned another embodiment of the present invention will be further clarified by way of examples, but the present invention is by no means limited to such examples. Also the used reagents are commercially available ones of high purity, unless otherwise specified. Also the contents already explained in the foregoing examples 7 and 8 will not be explained further for the purpose of simplicity.

EXAMPLE 9

500 parts by mass of cellulose (KC Flock W-100; supplied by Nippon Paper Co.) were put into 15,050 parts by mass of an enzyme solution and agitated for 8 hours at 45° C. The enzyme solution was prepared by dissolving 50 parts by mass of cellulase (Meicellase TP60; supplied by Meiji Seika Co.) in 15,000 parts by mass of aqueous solution of acetic acid/sodium acetate (pH 4.5). After the reaction, 1,000 parts by mass of methanol were added, then the water-soluble residue was filtered off and the solution was passed through a column of the ion exchange resin (Amberlite IR-120B, supplied by Organo Co.) and the solvent was distilled off. Then the reaction mixture was separated and purified to obtain 300 parts by mass of glucose.

The $^{13}$C-NMR (100 MHz, DMSO-$d_6$) of the synthesized glucose was measured with FT-NMR DPX400 (manufactured by Bruker Inc.). As a result, there were confirmed the following peak δ values resulting from α-type glucose: 92.12 ppm, 73.04 ppm, 72.29 ppm, 71.80 ppm, 70.58 ppm and 61.20 ppm; and those resulting from β-type glucose: 96.79 ppm, 76.70 ppm, 76.59 ppm, 74.78 ppm, 70.30 ppm and 61.00 ppm.

Then, 8,000 parts by mass of a 12% aqueous solution of barium carbonate were saturated with carbon dioxide, and 330 parts by mass of bromine and 300 parts by mass of the glucose obtained above were added and agitated for 30 minutes at 25° C. to obtain 250 parts by mass of gluconolactone represented by the following chemical formula (III):

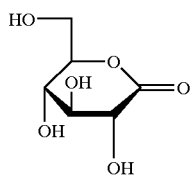

(III)

The $^{13}$C-NMR (100 MHz, DMSO-$d_6$) of the synthesized gluconolactone was measured to obtain the following δ values: 171.88 ppm, 81.23 ppm, 73.79 ppm, 71.43 ppm, 67.82 ppm and 60.14 ppm.

87 parts by mass of red phosphorus and 250 parts by mass of the gluconolactone were added to 12,000 parts by mass of hydroiodic acid (55 mass %), and were refluxed for 20 hours. The reaction mixture was filtered, then the filtrate was extracted with ether and the extract was washed with a 5% aqueous solution of sodium hydrosulfite. After the solvent ether was distilled off, distillation under a reduced pressure was executed to obtain 147 parts by mass of caproic acid. The $^{13}$C-NMR (100 MHz, CDCl$_3$) of the caproic acid was measured to obtain the following δ values: 13.90 ppm, 22.42 ppm, 24.51 ppm, 31.36 ppm, 34.22 ppm and 180.79 ppm.

147 parts by mass of the obtained caproic acid and an equivalent amount of N-chlorodiisopropylamine were added to 1,000 parts by mass of 84% sulfuric acid and were reacted for 5 hours at 25° C. to obtain 177 parts by mass of 5-chlorocaproic acid. Then 177 parts by mass of the 5-chlorocaproic acid were boiled with an aqueous solution of an equivalent amount of sodium hydroxide to obtain 129 parts by mass of δ-caprolactone. The $^{13}$C-NMR (100 MHz, CDCl$_3$) of the synthesized δ-caprolactone was measured to obtain the following δ values: 19.90 ppm, 20.88 ppm, 34.27 ppm, 35.31 ppm, 70.44 ppm and 172.84 ppm.

129 parts by mass of the δ-caprolactone were heated to 155° C. in a nitrogen atmosphere, and 0.39 parts by mass of tri-iso-propoxy-aluminum and 0.77 parts by mass of diethylene glycol were added to execute ring-opening polymerization thereby obtaining aliphatic polyester. The polymerization time was 10 hours, and the obtained aliphatic polyester showed a weight-average molecular weight of 290,000.

The $^{13}$C-NMR (100 MHz, CDCl$_3$) of the synthesized aliphatic polyester was measured to obtain the following 6 values: 19.95 ppm, 20.82 ppm, 34.46 ppm, 35.26 ppm, 70.31 ppm and 173.37 ppm, thereby confirming that the desired aliphatic polyester was synthesized.

EXAMPLE 10

300 parts by mass of glucose, obtained in the same manner as in the example 9, were oxidized and hydrolyzed in 2,500 parts by mass of 13.5 mol/l sulfuric acid saturated with bromine to obtain 290 parts by mass of gluconic acid represented by the following chemical formula (IV):

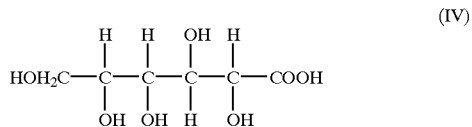

(IV)

100 parts by mass of red phosphorus and 290 parts by mass of the obtained gluconic acid were added to 14,000 parts by mass of hydroiodic acid (55 mass %) and were refluxed for 20 hours. Then the subsequent process was conducted in the same manner as in the example 9 to obtain 155 parts by mass of caproic acid.

155 parts by mass of the caproic acid and an equivalent amount of N-chlorodiisopropylamine were added to 1,000 parts by mass of 84% sulfuric acid and were reacted for 5 hours at 25° C. to obtain 187 parts by mass of 5-chlorocaproic acid. 187 parts by mass of the 5-chlorocaproic acid were boiled with an aqueous solution of an equivalent amount of sodium hydroxide to obtain 136 parts by mass of δ-caprolactone.

136 parts by mass of the obtained δ-caprolactone were heated to 160° C. in a nitrogen atmosphere, and 0.41 parts by mass of di-iso-propyl zinc and 0.82 parts by mass of 1,4-butanediol were added to execute ring-opening polymerization thereby obtaining aliphatic polyester. The polymerization time was 10 hours, and the obtained aliphatic polyester showed a weight-average molecular weight of 220,000. Also the measurement of $^{13}$C-NMR provided spectra similar to those in the example 9, confirming that the desired aliphatic polyester was synthesized.

EXAMPLE 11

Recycled paper for PPC (EN-500, A4: Canon Sales Co.), after use (copied on one side in a copying apparatus), was cut into 5 mm squares, and 500 parts by mass of such cut paper were put into 15,050 parts by mass of an enzyme solution and agitated for 10 hours at 45° C. The enzyme solution was prepared by dissolving 50 parts by mass of cellulase (Meicellase TP60; supplied by Meiji Seika Co.) in 15,000 parts by mass of an aqueous solution of acetic acid/sodium acetate (pH 4.5). After the reaction, 1,000 parts by mass of methanol were added, then the water-soluble residue was filtered off and the solution was passed through a column of the ion exchange resin (Amberlite IR-120B, supplied by Organo Co.) and the solvent was distilled off. Then the reaction mixture was separated and purified to obtain 280 parts by mass of glucose.

7,500 parts by mass of a 12% aqueous solution of barium carbonate were saturated with carbon dioxide, and 300 parts by mass of bromine and 280 parts by mass of the obtained glucose were added and agitated for 30 minutes at 25° C. to obtain 230 parts by mass of gluconolactone.

80 parts by mass of red phosphorus and 230 parts by mass of the obtained gluconolactone were added to 11,000 parts by mass of hydroiodic acid (55 mass %), and were thereafter processed in the same manner as in the example 9 to obtain 135 parts by mass of caproic acid.

135 parts by mass of the caproic acid were added to 1,000 parts by mass of 84% sulfuric acid and an equivalent amount of N-chlorodiisopropylamine and were reacted for 5 hours at 25° C. to obtain 163 parts by mass of 5-chlorocaproic acid.

163 parts by mass of the obtained 5-chlorocaproic acid were boiled with an aqueous solution of an equivalent amount of sodium hydroxide to obtain 118 parts by mass of δ-caprolactone.

Thereafter 118 parts by mass of the δ-caprolactone were heated to 150° C. in a nitrogen atmosphere, and 0.36 parts by mass of tetra-n-butoxy-titanium and 0.71 parts by mass of 1,8-octane-diol were added to execute ring-opening polymerization thereby obtaining aliphatic polyester. The polymerization time was 10 hours, and the obtained aliphatic polyester showed a weight-average molecular weight of 260,000.

The measurement of $^{13}$C-NMR provided spectra similar to those in the example 9, thus confirming that the desired aliphatic polyester was synthesized.

EXAMPLE 12

280 parts by mass of glucose, obtained in the same manner as in the example 11, were oxidized and hydrolyzed in 2,300 parts by mass of 13.5 mol/l sulfuric acid saturated with bromine to obtain 270 parts by mass of gluconic acid.

95 parts by mass of red phosphorus and 270 parts by mass of the gluconic acid were added to 13,000 parts by mass of hydroiodic acid (55 mass %) and were refluxed for 20 hours. Then the subsequent process was conducted in the same manner as in the example 9 to obtain 144 parts by mass of caproic acid.

144 parts by mass of the obtained caproic acid were added to 1,000 parts by mass of 84% sulfuric acid and an equivalent amount of N-chlorodiisopropylamine and were reacted for 5 hours at 25° C. to obtain 173 parts by mass of 5-chlorocaproic acid.

173 parts by mass of the 5-chlorocaproic acid were boiled with an aqueous solution of an equivalent amount of sodium hydroxide to obtain 126 parts by mass of δ-caprolactone.

Thereafter 126 parts by mass of δ-caprolactone were heated to 155° C. in a nitrogen atmosphere, and 0.37 parts by mass of tetra-t-butoxy-zirconium and 0.74 parts by mass of methanol were added to execute ring-opening polymerization thereby obtaining aliphatic polyester. The polymerization time was 9 hours, and the obtained aliphatic polyester showed a weight-average molecular weight of 180,000. The measurement of $^{13}$C-NMR provided spectra similar to those in the example 9, confirming that the desired aliphatic polyester was synthesized.

Evaluation of Physical Properties

The aliphatic polyesters synthesized in the examples 9 to 12 were subjected to evaluation of various physical properties, of which results are shown in Table 4. Also as a reference example 4, Celgreen (polycaprolactone plastic P-H7 manufactured by Daicel Chemical Industries, Co.) was included in the comparative evaluation.

TABLE 4

|  | Example 9 | Example 10 | Example 11 | Example 12 | Reference Example 4 |
|---|---|---|---|---|---|
| Tensile yield strength (JIS) K7113 Pa | 0.30 | 0.26 | 0.28 | 0.23 | 0.20 |
| Tensile modulus (JIS) K7113 Pa | 2.50 | 2.40 | 2.47 | 2.31 | 2.25 |
| Bending strength (JIS) K7203 Pa | 0.50 | 0.45 | 0.48 | 0.41 | 0.37 |
| Bending modulus (JIS) K7203 Pa | 5.10 | 4.86 | 4.96 | 4.65 | 4.41 |

These results indicate that the aliphatic polyesters synthesized in the examples 9 to 12 have physical properties equivalent or superior to those of the aliphatic polyester P-H7 of Daicel Chemical of the reference example 4 which is excellent in the strength and elongation, and can therefore be satisfactorily used as a substitute for the conventionally known plastics derived from petroleum.

As explained in the foregoing, the present invention enables to produce aliphatic polyester by the ring-opening polymerization of δ-caprolactone obtained from cellulose via glucose, and such aliphatic polyester has sufficient physical properties such as mechanical strength and can be utilized as a substitute for conventional plastic molded products. Furthermore, this finding opens up a way for utilizing cellulose as an efficient resource in obtaining plastics of high quality from cellulose as a starting material. In addition to starch and cellulose explained in the foregoing, glucans include glycogen, charonin, laminaran, dextran etc. which can also be utilized by those skilled in the art in methods similar to those in the aforementioned examples.

Also in a method different from the aforementioned invention, it is possible to produce aliphatic polyester utilizing caproic acid obtained from cellulose and starch via glucose, namely to obtain high-quality plastics utilizing cellulose and starch as the starting material.

Such method is a method for producing aliphatic polyester by ring-opening polymerization of caprolactones, the method being featured in that the caproic acid, constituting a precursor of the caprolactones, is synthesized by bacterial fermentation of glucose.

More specifically, there is provided a method for producing an aliphatic polyester represented by the following formula (I):

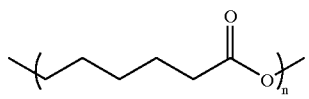  (I)

(wherein n stands for an integer within a range from 5 to 10,000), the method comprising the steps of:
- hydrolyzing cellulose or starch to obtain glucose;
- executing bacterial fermentation of the glucose to obtain caproic acid;
- chlorinating the caproic acid to obtain 6-chlorocaproic acid;
- cyclizing the 6-chlorocaproic acid to obtain ε-caprolactone; and
- executing ring-opening polymerization of the ε-caprolactone.

There is also provided a method for producing an aliphatic polyester represented by the following formula (VI):

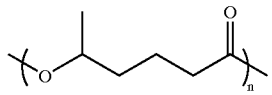  (VI)

(wherein n stands for an integer within a range from 5 to 10,000), the method comprising the steps of:
- hydrolyzing cellulose or starch to obtain glucose;
- executing bacterial fermentation of the glucose to obtain caproic acid;
- chlorinating the caproic acid to obtain 5-chlorocaproic acid;
- cyclizing the 5-chlorocaproic acid to obtain δ-caprolactone; and
- executing ring-opening polymerization of the δ-caprolactone.

These methods provide a method for producing caproic acid featured by bacterial fermentation of glucose.

The preferred bacteria to be used are aerophobic bacteria, the preferred aerophobic bacteria are those of Propionibacterium family, and the preferred bacteria of Propionibacterium family are Propionibacterium acnes CAP103 FERM P-18374 strain capable of producing caproic acid from glucose.

The aforementioned methods are capable, by utilizing bacteria, of efficiently converting glucose into caproic acid of such a high purity usable as the precursor of monomers (caprolactones) of aliphatic polyesters.

As a result, it is rendered possible to produce aliphatic polyesters utilizing caproic acid obtained from cellulose and starch via glucose, namely to obtain high-quality plastics from cellulose and starch as the starting material. It is thus rendered possible to produce aliphatic polyesters from waste cellulose and waste starch as the raw material, and to recycle cellulose and starch as a resource.

The raw material cellulose in obtaining glucose from cellulose can be not only commercially available cellulose but also recycled cellulose obtained by suitably processing waste paper or wood such as waste timbers. Consequently, the present invention opens up a new way for recycling waste cellulose as a resource.

Also the raw material starch in obtaining glucose from starch can be not only commercially available starch but also recycled starch obtained by suitably processing potato, sweet potato, corn etc. Consequently, the present invention opens up a new way for recycling waste starch as a resource.

What is claimed is:

1. A method of producing an aliphatic polyester represented by the following formula (I):

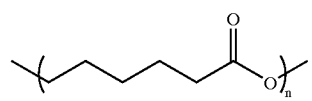  (I)

wherein n stands for an integer with a range of 5 to 10,000, the method comprising the steps of:

(i) hydrolyzing starch to obtain glucose;
(ii) oxidizing said glucose to obtain gluconolactone;
(iii) reducing said gluconolactone to obtain caproic acid;
(iv) chlorinating said caproic acid to obtain 6-chlorocaproic acid;
(v) cyclizing said 6-chlorocaproic acid to obtain ε-caprolactone represented by the following formula (II):

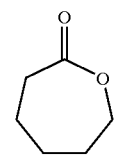  (II)

and (vi) executing ring-opening polymerization of said ε-caprolactone.

2. A method of producing an aliphatic polyester represented by the following formula (I):

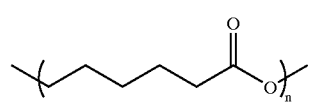  (I)

wherein n stands for an integer with a range of 5 to 10,000, the method comprising the steps of:

(i) hydrolyzing starch to obtain glucose;
(ii) oxidizing said glucose to obtain gluconic acid;
(iii) reducing said gluconic acid to obtain caproic acid;
(iv) chlorinating said caproic acid to obtain 6-chlorocaproic acid;
(v) cyclizing said 6-chlorocaproic acid to obtain ε-caprolactone represented by the following formula (II):

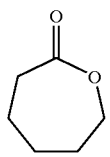

(II)

and (vi) executing ring-opening polymerization of said ε-caprolactone.

3. A method according to claim 1, wherein the step of obtaining glucose from starch is executed by hydrolysis utilizing an acid.

4. A method according to claim 1, wherein the step of obtaining gluconolactone from glucose is executed by bromine oxidation.

5. A method according to claim 2, wherein the step of obtaining gluconic acid from glucose is executed by oxidation utilizing bromine and concentrated sulfuric acid.

6. A method according to claim 1, wherein the step of obtaining caproic acid from gluconolactone is executed by a reducing reaction utilizing hydroiodic acid and red phosphorus.

7. A method according to claim 2, wherein the step of obtaining caproic acid from gluconic acid is executed by a reducing reaction utilizing hydroiodic acid and red phosphorus.

8. A method according to claim 1, wherein the step of obtaining 6-chlorocaproic acid from caproic acid is executed by a chlorination reaction utilizing chlorine and concentrated sulfuric acid.

9. A method according to claim 1, wherein the step of obtaining ε-caprolactone from 6-chlorocaproic acid is executed by a cyclization reaction utilizing an aqueous solution of sodium hydroxide.

10. A method according to claim 1, wherein the step of ring-opening polymerization of ε-caprolactone is executed by a ring-opening polymerization utilizing a polymerization catalyst and a polymerization initiator.

11. A method of producing an aliphatic polyester represented by the following formula (I):

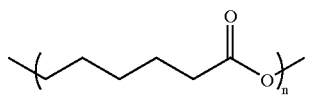

(I)

wherein n stands for an integer with a range of 5 to 10,000, the method comprising the steps of:

(i) hydrolyzing glucan to obtain glucose;
(ii) oxidizing said glucose to obtain gluconolactone;
(iii) reducing said gluconolactone to obtain caproic acid;
(iv) chlorinating said caproic acid to obtain 6-chlorocaproic acid;
(v) cyclizing said 6-chlorocaproic acid to obtain ε-caprolactone represented by the following formula (II):

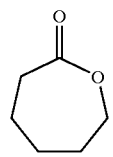

(II)

and (vi) executing ring-opening polymerization of said ε-caprolactone.

12. A method of producing an aliphatic polyester represented by the following formula (I):

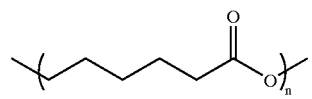

(I)

wherein n stands for an integer with a range of 5 to 10,000, the method comprising the steps of:

(i) hydrolyzing glucan to obtain glucose;
(ii) oxidizing said glucose to obtain gluconic acid;
(iii) reducing said gluconic acid to obtain caproic acid;
(iv) chlorinating said caproic acid to obtain 6-chlorocaproic acid;
(v) cyclizing said 6-chlorocaproic acid to obtain ε-caprolactone represented by the following formula (II):

(II)

and (vi) executing ring-opening polymerization of said ε-caprolactone.

13. A method according to claim 11, wherein the step of obtaining glucose from glucan is executed by hydrolysis utilizing an acid or an enzyme.

14. A method according to claim 11, wherein the step of obtaining gluconolactone from glucose is executed by bromine oxidation.

15. A method according to claim 12, wherein the step of obtaining gluconic acid from glucose is executed by oxidation utilizing bromine and concentrated sulfuric acid.

16. A method according to claim 11, wherein the step of obtaining caproic acid from gluconolactone is executed by a reducing reaction utilizing hydroiodic acid and red phosphorus.

17. A method according to claim 12, wherein the step of obtaining caproic acid from gluconic acid is executed by a reducing reaction utilizing hydroiodic acid and red phosphorus.

18. A method according to claim 11, wherein the step of obtaining 6-chlorocaproic acid from caproic acid is executed by a chlorination reaction utilizing chlorine and concentrated sulfuric acid.

19. A method according to claim 11, wherein the step of obtaining ε-caprolactone from 6-chlorocaproic acid is executed by a cyclization reaction utilizing an aqueous solution of sodium hydroxide.

20. A method according to claim 11, wherein the step of ring-opening polymerization of ε-caprolactone is executed by a ring-opening polymerization utilizing a polymerization catalyst and a polymerization initiator.

21. A method according to claim 11, wherein said glucan is cellulose.

22. A method of producing an aliphatic polyester represented by the following formula (VI):

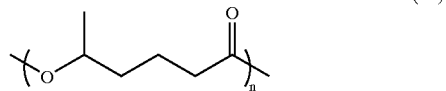
(VI)

wherein n stands for an integer with a range of 10 to 6,000, the method comprising the steps of:
(i) hydrolyzing glucan to obtain glucose;
(ii) oxidizing said glucose to obtain gluconolactone or gluconic acid;
(iii) reducing said gluconolactone or gluconic acid to obtain caproic acid;
(iv) chlorinating said caproic acid to obtain 5-chlorocaproic acid;
(v) cyclizing said 5-chlorocaproic acid to obtain δ-caprolactone; and
(vi) executing ring-opening polymerization of said δ-caprolactone.

23. A method according to claim 22, wherein the step of obtaining glucose from glucan is executed by hydrolysis utilizing an acid or an enzyme.

24. A method according to claim 22, wherein the step of obtaining gluconolactone or gluconic acid from glucose is executed by bromine oxidation.

25. A method according to claim 22, wherein the step of obtaining caproic acid from gluconolactone or gluconic acid is executed by a reducing reaction utilizing at least hydroiodic acid and red phosphorus.

26. A method according to claim 22, wherein the step of obtaining 5-chlorocaproic acid from caproic acid is executed by a chlorination reaction utilizing at least N-chlorodiisopropylamine and concentrated sulfuric acid.

27. A method according to claim 22, wherein the step of obtaining δ-caprolactone from 5-chlorocaproic acid is executed by a cyclization reaction utilizing at least an aqueous solution of sodium hydroxide.

28. A method according to claim 22, wherein the step of obtaining aliphatic polyester from δ-caprolactone is executed by a ring-opening polymerization utilizing at least a polymerization catalyst and a polymerization initiator.

29. A method according to claim 22, wherein said glucan is starch.

30. A method according to claim 22, wherein said glucan is cellulose.

* * * * *

UNITED STATES PATENT AND TRADEMARK OFFICE
CERTIFICATE OF CORRECTION

PATENT NO. : 6,559,275 B2
DATED : May 6, 2003
INVENTOR(S) : Masato Minami et al.

It is certified that error appears in the above-identified patent and that said Letters Patent is hereby corrected as shown below:

Column 2,
Line 40, "formula" should read -- formula (II): --.

Column 5,
Line 6, "The 5" should read -- The --.

Column 13,
Line 5, "hydrolodic" should read -- hydroiodic --.

Column 16,
Line 44, "eight" should read -- weight --; and
Line 47, "the another" should read -- another --.

Column 17,
Line 3, "δ-type" should read -- β-type --.

Column 20,
Line 8, "δvalues:" should read -- δ values: --; and
Line 19, "following 6" should read -- following δ --.

Signed and Sealed this

Sixteenth Day of December, 2003

JAMES E. ROGAN
*Director of the United States Patent and Trademark Office*